United States Patent [19]
Reinhard et al.

[11] Patent Number: 6,139,825
[45] Date of Patent: Oct. 31, 2000

[54] USE OF EXTRACTS FROM SAGE FOR PRODUCING A DEODORIZING PREPARATION

[75] Inventors: Max Reinhard, Bad Homburg; Jürgen Geissler, Dresden, both of Germany

[73] Assignee: Heilmittelbetreib Isernhagen GmbH, Germany

[21] Appl. No.: 09/441,442

[22] Filed: Nov. 17, 1999

[30] Foreign Application Priority Data

Nov. 19, 1998 [EP] European Pat. Off. ............. 98121938

[51] Int. Cl.⁷ ............................ A61K 7/32; A61K 35/78; A61K 7/00
[52] U.S. Cl. .................... 424/65; 424/195.1; 424/400; 424/401
[58] Field of Search .............. 424/65, 400, 401, 424/195.1

[56] References Cited

U.S. PATENT DOCUMENTS

| | | | |
|---|---|---|---|
| 4,459,285 | 7/1984 | Grollier et al. | 424/65 |
| 4,942,033 | 7/1990 | Aubert et al. | 424/195.1 |
| 5,660,831 | 8/1997 | Reinhard | 424/175.1 |

FOREIGN PATENT DOCUMENTS

| | | |
|---|---|---|
| 2 345 143 | 10/1977 | France . |
| 2 535 203 | 5/1984 | France . |
| 2 753 374 | 3/1988 | France . |
| 195 41 735 | 5/1997 | Germany . |
| 83 173 | 6/1981 | Luxembourg . |
| WO 94/17814 | 8/1994 | WIPO . |

OTHER PUBLICATIONS

"Verwendung von Herbasol–Extrakten in der Kosmetik", Seife–Oele–Fette–Wachse, publ. 107, No. 20, Dec. 1981, pp. 623–625.

STN Karlsruhe, DE, Database Chemical XP002096994, abstract, publ. 121, An=91368.

Database WPI, week 8616, Derwent Publ. Ltd., London, GB; AN 86–104817, XP002096995 & RO 88 082 A.

Database WPI, wk. 8929, Derwent Publ. Ltd., London, GB; AN 89–209302; XP002096996 & JP 01 145063 (LION).

*Primary Examiner*—Shelley A. Dodson
*Attorney, Agent, or Firm*—Birch, Stewart, Kolasch & Birch, LLP

[57] ABSTRACT

A use of extracts from flowers and/or leaves of sage (*Salvia officinalis*) obtained by a $CO_2$ extraction process for producing a deodorizing preparation e.g. a deodorant stick or a roll-on deodorant is described.

4 Claims, No Drawings

USE OF EXTRACTS FROM SAGE FOR PRODUCING A DEODORIZING PREPARATION

The invention relates to the use of extracts from flowers and/or leaves of *Salvia officinalis* (sage) for producing a deodorizing preparation. The invention also relates to a deodorizing preparation in which the active ingredient is an extract from flowers and/or leaves of sage.

It is known from "Lehrbuch der biologisches Heilmittel" by Dr. Gerhard Madeus (1938), page 2406 that *Salvia officinalis* (sage) is an effective substance for regulating secretions, especially the secretion of sweat. Further from "Rompp Chemielexikon", 9th edition (1993), page 211 it is known that sage has an anti-hidrotic effect i.e. it has an inhibiting effect upon the development of sweat. It is further known from U.S. Pat. No. 4,942,033 that a mixture of extracts from Butcher's broom (*Ruscus aculeatus* L.) and sage (*Salvia officinalis*) is effective in reducing capillary permeability and can thus inhibit the discharge of sweat. The effectiveness of extracts from flowers of *Salvia officinalis* in combating circulatory disorders is known from U.S. Pat. No. 5,660,831.

Accordingly it has been known so far to utilise the adstringent effect of sage in order to keep the sweat producing pores closed as much as possible and thereby prevent the occurrence of body sweat. However, none of the known preparations is able to suppress the build-up of sweat fully or at least to a significant extent so that hitherto the production of a residual amount of sweat could not be prevented thus resulting in the creation of unpleasant sweaty odours.

Bodily sweat per se is odourless and it is only the bacterial breakdown of the sweaty secretions that leads to the creation of unpleasant odours. Deodorising preparations exhibiting an anti-bacterial effect have been developed for the purpose of preventing a breakdown of the sweaty secretions from producing dour. A disadvantage of such preparations is that their effects upon a multitude of bacterial types are relatively non-specific and so could adversely affect the skin's natural and desirable bacterial flora.

An object of the invention is to produce an improved deodorizing preparation. Another object of the invention is to produce a deodorizing preparation which fully, or at least to a great extent, is able to suppress the build-up of sweat fully or at least to a great extent. Still another object of the invention is to produce a deodorizing preparation which has a specific effect basically on only those bacteria responsible for breaking down sweaty secretions and thereby creating the odours.

According to the present invention these and other objects are achieved by use of an extract from flowers and/or leaves of *Salvia officinalis* obtained by a $CO_2$ extraction process for producing a deodorizing preparation.

In the investigations of sage extracts carried out within the framework of the invention, the surprising discovery was made that such extracts from *Salvia officinalis* not only possess an anti-hidrotic effect, but that they also have a selective bactericide effect upon the bacteria responsible for breaking down sweat and thereby creating the odours.

A further aspect of the invention is in a deodorizing preparation containing an extract from flowers and/or leaves of *Salvia officinalis* as the active ingredient, together with conventional carrier substances and/or dilutants. This preparation may be provided e.g. in the form of sprays, tinctures, powders and the like. A particularly preferred way of administering it is in the form of a deodorant stick or a so-called roll-on deodorant.

The process of extracting flowers or leaves of plants is an art per se known to an expert and needs not be explained in furher deatils. A supercritical carbon dioxide ($CO_2$) extraction process is preferred for the purpoese of the present invention. The use of supercritical $CO_2$ in the process of extraction from flowers and/or leaves of *Salvia officinalis* (sage) can be carried out at low temperatures and is a particularly gentle process. The content of extract from sage i.e. the content of active ingredient in the deodorizing preparation, preferably amounts to between 0.5 and 5%.

The temperature during extraction, and in any subsequent stage required for at least partial removal of the extractant such as by distillation for example, should be 50° C. or less and preferably 40° C. or less, so as to prevent thermal impairment of the constituents of the flowers and/or leaves. In the case of distillative separation, this means that the pressure must be reduced to an extent necessary for maintaining the above-mentioned upper temperature limit.

Extraction using supercritical $CO_2$ may be effected in any apparatus suitable therefor. The lower limits for the temperature and pressure during the extraction process arise from the thermodynamic properties of $CO_2$, namely, a critical temperature of 31.3° C. and a critical pressure of 71.5 bar. In particular, it is preferred to work at a temperature of 40° C. or below when extracting with $CO_2$. The pressure should preferably lie in the range from 90 to 300 bar. Extraction may be continued until all of the constituents extractable from the leaves and flowers of *Salvia officinalis* by using supercritical $CO_2$ have been extracted therefrom. This is usually the case for this extraction process after a period of 1 to 2 hours. However, in accordance with the invention, it is possible to extract just a portion of the constituents of the leaves and flowers of *Salvia officinalis*.

One advantage of using supercritical $CO_2$ as the extractant, as compared to the use of other extractants such as ethanol or water, is that extraction can be effected at temperatures below 40° C., whereas a conventional extraction process using alcohol for example requires the ethanol to be distilled off at temperatures of more than 100° C. A further advantage of extracting with supercritical $CO_2$ is that solventless extracts can be obtained. This thus avoids the effect of the extract from being unduly affected by solvents such as ethanol.

After harvesting, the flowers and leaves of *Salvia officinalis* are preferably dried i.e. at a temperature of 40° C. or below. Just as for the extraction temperature, a comparatively low drying temperature is chosen so as to permit the yield from the crop to be treated in a gentle manner. It is also feasible to utilise deep frozen sage.

The extract from the flowers and/or leaves of *Salvia officinalis* obtained by the method in accordance with the invention has a paste-like consistency. This extract may be used as the effective constituent of a deodorizing preparation. This preparation may be provided in any form in which it can be administered. For this purpose, the extract is charged with any suitable thinner, filler or the like and then converted into the wanted administrable form. There are no special restrictions in regard to the ratio of the extract and the thinner, filler or the like. Production of the preparation can be effected in accordance with conventional cosmetic practices.

The invention will now be explained in more detail hereinafter by means of examples.

EXAMPLE 1

This example concerns the production of a $CO_2$-induced, total extract. For this purpose, hand-picked, dried flowers of

*Salvia officinalis* were extracted for 2 hours at a pressure of 300 bar (total extraction) and a temperature of 40° C. using $CO_2$. 623 g of extract were obtained thereby from 15.2 kg of sage flowers. This corresponds to an extract yield of 4.1%. The extract obtained was in the form of a paste.

EXAMPLE 2

This example is concerned with obtaining a $CO_2$-induced, selective extract. The extraction conditions comprised an extraction period of 2 hours, a pressure of 90 bar (selective extraction) and a temperature of 40° C. 14 g of extract were obtained thereby from the 1.7 kg of dried flowers of *Salvia officinalis* being used. This corresponds to an extract yield of 0.8%. The extract obtained was in the form of a paste.

EXAMPLE 3

This was conducted as in the above example 1 except that sage leaves were used instead of sage flowers. A total extract was obtained with a yield similar to that of example 1.

The following Examples 4 and 5 illustrate the composition of the deodorizing preparations, whereby INCI nomenclature is used to describe the constituents.

EXAMPLE 4

Sage roll-on deodorant emulsion:

Constituents: acqua, glyceryl stearate, cetearyl alcohol, paraffinum liquidum, *Salvia officinalis*, ceteareth-25, ceteareth-12, methyldibromoglutaronitrile, phenoxyethanol.

EXAMPLE 5

Sage roll-on deodorant gel:

Constituents: acqua, alcohol denat., PEG-7 glyceryl cocoate polymer, *Salvia officinalis*, PEG-35, castor oil, hydroxyethylcellulose.

The following Example 6 is concerned with an in-vitro test of the sage extracts.

EXAMPLE 6

The influence of sage extracts on sweat-decomposing bacteria was investigated. For this purpose, dilutions of the preparations from Examples 1 to 3 were produced in a mixture comprising 72% propylenglycol, 21% water and 7% sodium stearate.

The tests were carried out as follows: A depression was formed in the centre of a culture medium base (in a Petri dish). A sheet of filter paper soaked with the test solution was placed in the depression. The sheet was then covered with a culture medium up to the level of the rest of the agar surface. After the agar had set, the base was inoculated with various microorganisms with the aid of an ose. The bacterial colonies at the contacting surface between the culture medium and the sheet of paper were investigated.

The bacterial growth was assessed in the following manner:
A: An indication of the radius of the inhibition zone measured from the edge of the loaded flake,
B: Total inhibition of growth on the contacting surface,
C: Minimum growth (thin layer) on and at the edge of the contacting surface,
D: Growth on the contacting surface corresponding to the negative control.

The results of this assessment are listed in the following table. This shows for example, that a 1% selective-extract solution of sage flowers has a significant growth-inhibiting effect on the microbes responsible for breaking-down the sweat and thus for creating the odours, namely, *Staphylococcus aureus, Staphylococcus epidermidis* and *Corynebacterium spec.* On the other hand, the growth of numerous other microbes, some being typical for the skin, remained uninhibited. The advantage of the preparation in accordance with the invention thus lies, inter alia, in that sweat-decomposing bacteria are selectively inhibited whilst the other microorganism flora are, for the most part, unaffected.

TABLE

| Extract from Example | 2 | 1 | 3 | 3 |
|---|---|---|---|---|
| Concentration | 1% | 1% | 0.6% | 1.0% |
| Type of microbe | | | | |
| *Staphylococcus aureus* | A: 1 mm | A: 2 mm | C | B |
| *Staphylococcus epidermidis* | A:1–2 mm | A:2–3 mm | C | B |
| *Corynebacterium spec.* | A: 6 mm | A: 2–3 mm | A: 3 mm | A: 1 mm |
| *Escherichia coli* | D | D | D | D |
| *Proteus vulgaris* | D | A: 1–2 mm | D | |
| *Klebsiella pneumoniae* | D | D | D | D |
| *Enterobacter aerogenes* | D | D | D | D |
| *Pseudomonas aeruginosa* | D | D | D | D |
| *Pseudomonas fluorescens* | D | A: 1 mm | D | D |
| *Lactobacillus acidophilus* | A: 2 mm | A: 2 mm | D | D |
| *Peptostreptococcus prevotii* | —* | — | D | B |
| *Candida albicans* | D | D | D | D |
| *Aspergillus niger* | D | D | D | D |

*—: not determined

What is claimed is:

1. A process for producing a deodorizing preparation having specific effects on growth of bacteria responsible for breaking down sweaty secretions comprising the steps of providing an extract of *Salvia officinalis* as an active ingredient of the preparation by a $CO_2$-extraction from a *Salvia-officinalis* plant at a temperature of about 50° C. or less and a pressure in a range of 90 to 300 bar, adding to said extract a conventional ingredient of a group comprising conventional carrier substances and dilutants, mixing said extract and said conventional ingredient, and administering the mixture in the form of a deodorant dispenser.

2. The process according to claim 1, wherein the extraction is prepared from the flowers of *Salvia officinalis*.

3. A deodorizing preparation having specific effects on the growth of bacteria responsible for breaking down sweaty secretions comprising an extract of *Salvia officinalis* as an active ingredient of the preparation and obtained by a $CO_2$-extraction of a *Salvia-officinalis* plant at a temperature of about 50° C. or less and a pressure in a range of 90 to 300 bar, and a conventional ingredient of a group comprising conventional carrier substances and dilutants.

4. The preparation according to claim 3, wherein the extraction is obtained from the flowers of *Salvia officinalis*.

* * * * *